US006559183B1

(12) United States Patent
Schmid et al.

(10) Patent No.: US 6,559,183 B1
(45) Date of Patent: May 6, 2003

(54) NANO-EMULSION OF 5-AMINOLEVULINIC ACID

(75) Inventors: Hans W. Schmid, Zug (CH); Gerd Burmeister, Oberarth (CH)

(73) Assignee: ASAT AG Applied Science & Technology, Zug (CH)

( * ) Notice: Subject to any disclaimer, the term of this patent is extended or adjusted under 35 U.S.C. 154(b) by 0 days.

(21) Appl. No.: 09/831,564

(22) PCT Filed: Nov. 12, 1999

(86) PCT No.: PCT/EP99/08711

§ 371 (c)(1),
(2), (4) Date: Jul. 26, 2001

(87) PCT Pub. No.: WO00/28971

PCT Pub. Date: May 25, 2000

(30) Foreign Application Priority Data

Nov. 12, 1998 (DE) .......................................... 198 52 245

(51) Int. Cl.[7] ........................ A61K 9/07; A61K 31/197; A61K 41/00; B01F 3/08; G01N 21/64
(52) U.S. Cl. ........................ 514/561; 424/450; 436/64; 436/172; 514/863; 514/864; 516/56
(58) Field of Search ........................... 516/56; 424/450; 514/864, 863, 561; 436/172, 64; 607/89, 94, 901

(56) References Cited

U.S. PATENT DOCUMENTS

| 5,152,923 | A |   | 10/1992 | Weder et al. ........... 514/938 X |
| 5,407,808 | A | * | 4/1995  | Halling et al. ............. 436/64 X |
| 5,599,831 | A | * | 2/1997  | Poretz et al. ........... 424/450 X |
| 5,616,342 | A | * | 4/1997  | Lyons ......................... 424/450 |
| 5,753,241 | A | * | 5/1998  | Ribier et al. .............. 516/56 X |
| 6,034,267 | A | * | 3/2000  | Gierskcky et al. .......... 560/155 |
| 6,074,666 | A | * | 6/2000  | Desai et al. ................. 424/450 |

FOREIGN PATENT DOCUMENTS

| EP | 0 274 431 | 7/1988 |
| EP | 0 704 209 | 4/1996 |

OTHER PUBLICATIONS

Hürlimann et al., "Photodynamic therapy of superficial basal cell carcinomas using topical 5–aminolevulinic acid in a nanocolloid lotion", DERMATOLOGY, vol. 197, No. 3, 1998, pp. 248–254.

* cited by examiner

Primary Examiner—Richard D. Lovering
(74) Attorney, Agent, or Firm—Rothwell, Figg, Ernst & Manbeck

(57) ABSTRACT

The present invention relates to a composition comprising a nano-emulsion that contains 5-aminolevulinic acid as well as a carrier in an aqueous phase. This invention also relates to a pharmaceutical preparation containing this composition. The nano-emulsions of this type can be used in photodynamic therapy as well as in the photodiagnostic detection of proliferatives cells.

21 Claims, No Drawings

NANO-EMULSION OF 5-AMINOLEVULINIC ACID

This application is a 371 of PCT/EP99/08711 filed Nov. 12, 1999.

The present invention relates to nanoemulsions which contain 5-aminolevulinic acid or its derivatives, precursors or metabolites.

Photodynamic therapy is a novel and promising method for treating various premalignant and malignant diseases which are connected to cell proliferation. The principle of photodynamic therapy is based on introducing what is termed the photosensitizer into the tumor tissue and using irradiation with light of a suitable wavelength to convert this photosensitizer into a cytotoxically active compound which in the end destroys the cells. The selectivity of this method is based on the sensitizer being concentrated to a greater extent in rapidly proliferating tumor cells than in normal tissue. Irradiation with light in a locally restricted manner can then be used to specifically activate the sensitizer which is present in the tumor cells, thereby destroying the cancer cells while to a large extent sparing the healthy tissue.

Until now, an intravenously administered mixture of hematoporphyrin derivatives has in the main been used as the photosensitizer. Despite the encouraging clinical successes which have been achieved in connection with a number of different types of cancer, these hematoporphyrin derivatives nevertheless suffer from a variety of disadvantages. In the first place, relatively high concentrations of the active compound appear in normal tissue due to the low degree of tumor selectivity and the fact that the active compound is only slowly eliminated from the body. Undesirable photochemical reactions therefore take place in healthy tissue in connection with the irradiation. In the second place, this treatment results in a general sensitivity to light such that the patient is not allowed to expose himself to daylight for a period of some four weeks.

In certain cases, it is possible, particularly in connection with dermatological and gynecological applications, to bring about a reduction in the high concentration of active compound in normal tissue, and therefore in the undesirable side-effects, by developing topically applicable active compound formulations in place of the known systemic formulations. Attempts are also being made to reduce the sensitivity to light by using photosensitizer precursors which are photochemically inactive and are only converted into a photosensitizer within the target cell.

5-Aminolevulinic acid is an endogenous substance which is synthesized from glycine and succinyl-CoA. In heme biosynthesis, the extremely photoactive protoporphyrin IX is formed from 5-aminolevulinic acid (5-ALA) in several rapidly proceeding reactions steps, and is then converted into heme in a slow reaction. If the heme concentration is too high, a natural control mechanism inhibits both the endogenous synthesis of 5-aminolevulinic acid and the breakdown of protoporphyrin IX.

This control mechanism is circumvented by exogenously administering synthetically prepared 5-aminolevulinic acid, thereby giving rise to an increased production of protoporphyrin IX. Since the breakdown of protoporphyrin IX is still inhibited by the natural control mechanism, this compound becomes concentrated in the cells. When irradiated with light, protoporphyrin IX is able to enter into a photochemical oxidation reaction and consequently acts as a photosensitizer. When the sensitizer molecule absorbs a quantum of light, it is first of all transferred into an electronically excited state (singlet state), which is relatively short-lived, and either releases its excess energy once again within a few nanoseconds by emitting a fluorescence photon or else passes over into a relatively long-lived triplet state. Energy from this triplet state can be transferred to oxygen molecules which are present in the cell. The singlet oxygen which is formed in this connection has a cytotoxic effect, in particular on proliferating cells, since it reacts with cell components, for example the cell membrane and the mitochondria, or triggers the formation of cell-damaging free radicals. Furthermore, irradiation of the photosensitizer gives rise to a characteristic fluorescence radiation which can be used for detection reactions, for example for detecting proliferating cells.

A number of investigations using topically applicable 5-aminolevulinic acid compositions are known from the prior art. While these investigations have the feature in common that the 5-aminolevulinic acid employed is in the form of an oil-in-water emulsion, differences exist with regard to other parameters, such as period of penetration, period of treatment, type of light employed and the dose of light applied.

B. Thiele et al. (H+G, Volume 69, No. 3, pages 161–164 (1994)) describe investigations which involve using 20% δ-aminolevulinic acid in the form of an oil-in-water emulsion, with a penetration period of from 5 to 6 h, and subsequently irradiating with an argon ion-pumped dye laser (emission maximum 630 nm) giving a cumulative total dose of from 50 to 100 $J/cm^2$.

Wolf et al. (Journal of the American Academy of Dermatology Vol. 28, pages 17 to 21, 1993) describe investigations which involve using 20% 5-aminolevulinic acid in the form of an oil-in-water emulsion, with a penetration period of 4, 6 or 8 h, and irradiating with unfiltered light or red light, giving a light dose of from 30 $J/cm^2$ to 100 $J/cm^2$.

Although the investigations disclosed in the prior art clearly demonstrate the promising potential of photodynamic therapy using 5-aminolevulinic acid, oil-in-water emulsions which are so far known suffer from a number of disadvantages.

Thus, M. Novo Rodriguez et al. (SPIE, Vol. 2371, pages 204–209) showed that, in the high concentrations which are required for a clinical application, aminolevulinic acid is unstable in aqueous solutions in the neutral to basic pH range. In the time period of 25 h investigated, satisfactory results are only obtained at a pH of 5.01, and a concentration of 3% and a pH of 5 are specified as the optimal conditions for aqueous solutions of 5-aminolevulinic acid. However, for clinical use, it will in general also be necessary to provide compositions in a higher concentration range; furthermore, to be used commercially, the 5-ALA solutions have to be stable for a period which is of the order of weeks or months.

V. von Arx et al. (J. Pharm. Pharmacol. 49: 652–656, 1997) describe investigations relating to the topical application of 5-aminolevulinic acid in a variety of gels. This publication states that the best formulation for maintaining the stability of 5-aminolevulinic acid is a combination with Novion AA-1, a polyacrylic acid, at a pH <6.

Another disadvantage of the known oil-in-water emulsions is that the depth to which the photosensitizer penetrates into the damaged tissue is not optimal. As a result, the diseased tissue is in many cases only accessible to the photodynamic therapy in its superficial layers even though the depth to which the light employed for activating the photosensitizer penetrates would also enable more deeply lying layers to be treated.

The object of the present invention was therefore to make available 5-aminolevulinic acid-comprising compositions in which the disadvantages known from the prior art are at least partially eliminated and which, in particular, possess adequate stability and exhibit an improved ability to penetrate into tissue.

This object is achieved by a composition which is characterized in that it contains a nanoemulsion which comprises a substance selected from 5-aminolevulinic acid, or a derivative, a precursor and/or a metabolite thereof, and a carrier in an aqueous phase.

It was observed, surprisingly, that the stability of 5-aminolevulinic acid can be substantially increased when the acid is formulated into a nanoemulsion. While the reasons for this are not known, it appears that a microenvironment created by nanosomes has a particularly favorable effect on the stability of the 5-aminolevulinic acid.

It has furthermore been shown, surprisingly, that very high tissue penetration depths can be achieved with the nanoemulsions according to the invention, resulting in more deeply lying diseases, or diseases with higher layer thicknesses, also becoming accessible to treatment. The greater penetration depths were particularly surprising because it had previously been assumed that, due to its small size, 5-aminolevulinic acid would in any case be readily able to penetrate through a damaged epidermis which is present, for example, over inflammations, precancerous stages and tumors.

A third surprising advantage is that, when packed into nanosomes in accordance with the invention, 5-aminolevulinic acid is evidently taken up very efficiently by the cells. This firstly improves targeting; secondly, it means that the penetration period, i.e. the time between applying the composition and irradiating the diseased tissue with light, can be reduced, with this representing a distinct relief for the patient.

According to the invention, the nanoemulsion comprises an active substance which is selected from 5-aminolevulinic acid or a derivative, a precursor and/or a metabolite thereof. "Derivative" is to be understood as being, in particular, salts, complexes and addition compounds. "Precursor" and "metabolite" are in this connection to be understood as being those substances which are converted in a cell into protoporphyrin IX. Particular preference is given to the active substance being 5-aminolevulinic acid or one of its derivatives. The carrier can be any carrier as long as it is able to form the nanoemulsion in an aqueous phase. The carrier preferably comprises an oil phase, i.e. a material which is immiscible with water, for example lipids, and an emulsifier. Physiologically harmless carrier substances are expediently used.

The size of the emulsified particles in the nanoemulsion (nanosomes) is on average ≦200 nm, e.g. from 10 to 200 nm. The particle size which is in each case optimal depends on other parameters such as the viscosity of the composition. For example, good results were obtained with a gel having a viscosity of 5 mPas at an average particle diameter of about 110 nm, and also for a lotion having a viscosity of 1.6 mPas at an average particle diameter of about 20 nm.

Suitable carrier systems, which are stable over a long period of time, which do not contain any high concentrations of surfactants and cosurfactants, and which are free from toxic emulsifier complexes, are disclosed, for example, in U.S. Pat. No. 5,152,923. These nanoemulsions comprise a glycerophosphatide, such as a lecithin or a cephalin, as the emulsifier and physiologically tolerated lipids, e.g. triglycerides, such as vegetable or animal oils, for example groundnut oil, soybean oil, etc., as the oil phase. The emulsifier/oil weight ratio is from 0.05 to 0.4:1.

Examples of emulsifiers which have already been employed successfully in practice in 5-aminolevulinic acid nanoemulsions are egg lecithin, soybean lecithin and phosphatidyl choline. An example of an approved lipid is Miglyol 812.

The proportion of active substance, for example 5-aminolevulinic acid, in the composition essentially depends on the application which is envisaged. In general, from about 1 to 25% by weight, based on the total weight of the composition, are present. However, it is also possible to use higher or lower doses. A proportion of from 5 to 15% by weight, in particular of about 10% by weight, has proved to be suitable for applications in connection with photodynamic therapy.

The composition can additionally comprise adjuvants and/or additives, in particular those substances which are customary in cosmetics or pharmacy. Examples of such substances are buffers, stabilizers, additional emulsifiers, thickeners, etc.

In a particularly preferred embodiment, the composition according to the invention is a gel which, based on the total weight of the composition, comprises from 1 to 25% by weight, preferably from 5 to 15% by weight, of active substance, from 40 to 60% by weight, preferably from 45 to 55% by weight, of carrier and from 0 to 10% by weight, preferably from 1 to 5% by weight, of adjuvants, with the remainder being water.

According to another particularly preferred embodiment, the composition according to the invention is a lotion which, based on the total weight of the composition, comprises from 1 to 25% by weight, preferably from 5 to 15% by weight, of active substance, from 10 to 30% by weight, preferably from 15 to 25% by weight, of carrier and from 10 to 30% by weight, preferably from 15 to 25% by weight, of adjuvants, with the remainder being water.

As mentioned at the outset, the 5-aminolevulinic acid composition according to the invention exhibits a surprisingly high degree of stability on storage, with the proportion of active substance in the composition having a pH of between 1.5 and 3 preferably being reduced, after one year of storage at room temperature, by not more than 5% and, particularly preferably, by not more than 4%. After one year of storage at 5° C., the proportion of active substance is preferably reduced by not more than 3% and particularly preferably by not more than 2.5%.

The present invention also relates to the composition according to the invention which is in the form of a pharmaceutical preparation. In this case, the composition is free of constituents which are not pharmaceutically acceptable and preferably free of constituents which, for example, provoke irritation. In addition to the carrier substances which have already been mentioned, the pharmaceutical preparation can also comprise further adjuvants and/or additives which are acceptable and preferably well tolerated.

The pharmaceutical preparation can be present in a form which is suitable for systemic administration, such as an injectable liquid. However, for dermatological and gynecological applications, the the preparation is preferably in a form which is suitable for topical administration. The preparation possesses properties, e.g. viscosity and rheology, which are favorable for the administration form which is in each case required in order to ensure that, after the preparation has been administered, the nanosomes loaded with 5-aminolevulinic acid penetrate to an adequate extent into the target tissue. These viscosity and rheology properties can be adjusted by adding thickeners such as polyethylene glycol stearyl ethers, polyethylene glycol stearates and/or polysaccharides such as polysaccharide B-1459, for example.

The present invention also relates to a process for producing the composition or the pharmaceutical preparation according to the invention. In this process, the constituents of the carrier material are initially introduced in an aqueous phase and the mixture is converted into a nanoemulsion by homogenizing thoroughly. It is possible, for example, to use commercially available high pressure homogenizers for this purpose. The 5-aminolevulinic acid, and any additives which may be present, can be added before and/or after the homogenization. After the nanoemulsion has been prepared, it is then possible to add other adjuvants and additives whose presence was not desirable during the homogenization.

Preference is given to excluding air while carrying out the process, for example by means of applying a vacuum and/or a protective gas atmosphere. In addition, it is preferred to implement the process while excluding light. The process is carried out at a temperature at which the desired nanoemulsion can be formed and the constituents, in particular the active substance, is adequately stable. In general, it has been found that a temperature range of from about 5 to 45° C. is suitable. However, adjuvants and/or additives which are, for example, first of all mixed, and homogenized where appropriate, in a separate mixture, and only after that added to the composition, can be processed at higher temperatures, for example up to about 80° C. For a pharmaceutical application, care is taken to ensure that the resulting product is sterile, for example by employing sterile starting materials and maintaining sterile process conditions and/or by inserting a sterilization step after the preparation.

An important area of use for the compositions according to the invention is in the field of photodynamic therapy, with particular preference being given to applying the nanoemulsion topically. The nanoemulsion according to the invention can be used in association with all diseases whose control comprises inhibiting the proliferation of, or destroying, cells or tissues by photoactivating a sensitizer which is formed from 5-aminolevulinic acid. The diseases include, in particular, those which are associated with an increase in cell proliferation since, in this case, the photosensitizer is concentrated to a particularly high degree by the increased cell metabolism in diseased cells.

The compositions according to the invention are consequently suitable for treating tumor diseases such as basal cell carcinoma, squamous cell carcinoma, Bowen's disease, solar keratosis, condylomata acuminata (CIN), epithelial neoplasia of the vulva (VIN), and nodose and subcutaneous cancer diseases. Psoriasis is an example of a nontumorous disease.

The treatment is effected, for example, by topically applying a nanoemulsion which contains the active substance, e.g. 5-aminolevulinic acid, and then incubating in order to allow an adequate quantity of the 5-aminolevulinic acid to penetrate into the tissue which is being treated. During the incubation, irradiation of the treated area with light is preferably avoided, for example by covering it, in order to prevent any undesirable premature activation. After the incubation period, which is generally from about 1 to 8 h and usually about 4 h, has expired, the tissue is irradiated with an adequate dose of radiation using a light source. Suitable light sources include lamps which emit white light and also monochromatic light sources, such as a laser, in particular an argon dye laser which emits at about 630 nm. The radiation doses are normally in a range of from about 20 J/cm$^2$ to several hundred J/cm$^2$ per application.

Another area for using the nanoemulsions according to the invention relates to detecting the presence of proliferating cells in a sample, for example a tissue sample. The detection is based on selectively concentrating a photosensitizer, which is produced by metabolism of the active substance, in proliferating cells as compared with normal cells. Preference is given to the active substance being 5-aminolevulinic acid and the photosensitizer being protoporphyrin IX. The extent to which the photosensitizes has been concentrated can be determined by means of photodiagnostic methods, for example by irradiating with light having a wavelength of 405 nm and measuring the fluorescence radiation generated by the photosensitizer. The nanoemulsions according to the invention are particularly suitable for being used in tumor diagnosis.

The invention furthermore relates to the use of the nanoemulsion according to the invention for producing a drug for photodynamic therapy.

Finally, the invention relates to a kit which comprises a nanoemulsion according to the invention, which is suitable for being applied topically, and one or more auxiliary substances. Examples of these auxiliary substances are a covering material, such as a plastic film which is applied to the site being treated, after the nanoemulsion has been applied, in order to prevent premature activation by light, and means for attaching the covering material or else means for applying the nanoemulsion to the site being treated.

The following examples are intended to clarify the invention.

EXAMPLES

1. Preparing a 10% 5-Aminolevulinic Acid Lotion

A nanocolloid carrier system was prepared, in a phosphate buffer, from egg lecithin (83% phosphatidylcholine), Miglyol 812 (triglyceride) and Polysorbatum 80 using the method described in U.S. Pat. No. 5,152,923. The analytical data for the carrier system were as given in table 1.

TABLE 1

| | |
|---|---|
| Aqueous phase | 20 mM phosphate buffer, pH 6.0 |
| optical properties | yellow, highly iridescent liquid |
| pH at room temperature | 6.0 |
| viscosity (20° C.) | 1.6 mPas |
| size of the nanoparticles | ≦10–200 nm |
| average diameter | 19.4 nm |
| content of egg lecithin | 17.5 mg/ml |
| content of Polysorbatum 80 | ≦3% (w/w) |
| content of Miglyol 812 | 34–38 mg/ml |
| aerobic mesophilic organisms in 50 ml | <1 CFU/ml |

The components used for preparing a 5-ALA-nanocolloid lotion, and their relative proportions, are given in table 2.

TABLE 2

| Name | Quantity (% by weight) |
|---|---|
| Phase 1 | |
| Cetyl alcohol | 5.00% |
| Stearyl alcohol | 1.00% |
| Glycerol monostearate | 2.00% |
| SNOWWHITE vaseline grease | 2.00% |
| Pharm. perliquidum paraffin | 2.00% |
| Cosm. isopropyl myristate | 4.00% |
| Cremophor A 25 | 1.00% |
| Cremophor S9 | 1.50% |
| Cremophor EL 00647 | 1.88% |
| Phase 2 | |
| Water | 48.87% |
| Sorbitol, 70% | 0.25% |
| Phenoxyethanol | 0.50% |

TABLE 2-continued

| Name | Quantity (% by weight) |
|---|---|
| Phase 3 | |
| Nanocolloid (table 1) | 20.00% |
| 5-Aminolevulinic acid hydrochloride | 10.00% |

All the procedural steps were carried out while excluding light and atmospheric oxygen. Phase 1 was prepared by melting together, at 80° C., the components shown in table 2, in the given quantity ratios, and then mixing.

Phase 2 was prepared in a separate receptacle. For this, the water was introduced initially and the remaining components shown in table 2 were added while stirring. After it had been adequately mixed, phase 2 was heated to 80° C. and admixed with phase 1 in vacuo.

After it had been cooled down to 75° C., the mixture was homogenized for 2 min in a homogenizer. The resulting mixture was cooled down to 60° C. and homogenized once again for 2 min.

Phase 3 was prepared in a separate receptacle in vacuo and while excluding light. For this, the nanocolloid carrier system, as described above, was introduced initially and the 5-aminolevulinic acid hydrochloride was dissolved in it at from 25 to 30° C. Phase 3 was then added, at 40° C. and in vacuo, to the mixture of phases 1 and 2. After that, the composition was gassed with protective gas and homogenized for from 2 to 3 min in a homogenizer. It was then left to cool down to room temperature while being stirred.

In order to determine the long-term stability of the active compound, a portion of the lotion was subjected to a storage test. Following one year of storage at 5° C., the content of 5-ALA was 97.92% of the original content, while a value of 96.50% was obtained at room temperature over the same period of time.

2. Preparing a 10% 5-Aminolevulinic Acid Gel

A nanocolloid carrier system was prepared, in a K/Na phosphate buffer, from egg lecithin and Miglyol 812 (triglyceride) using the method described in U.S. Pat. No. 5,152,923. The analytical data were as given in table 3.

TABLE 3

| Aqueous phase | 20 mM phosphate buffer, pH 6.0 |
|---|---|
| optical properties | milky liquid |
| pH at room temperature | 6.0 |
| viscosity at 20° C. | 1.5 mPas |
| size of the nanoparticles | ≦10–200 nm |
| average diameter | 110.6 nm |
| standard deviation | 32.1% |
| content of total lipid | 105.4 mg/g |
| content of lecithin | 27.0 mg/g |
| content of Miglyol 812 | 78.4 mg/g |
| aerobic mesophilic organisms in 100 ml | <1 CFU/ml |

The components used for preparing a 5-aminolevulinic acid nanocolloid gel, and their relative proportions, are given in table 4.

TABLE 4

| Name | Quantity (% by weight) |
|---|---|
| Phase 1 | |
| Water | 38.30% |
| Keltrol | 1.70% |
| Phase 2 | |
| Nanocolloid (table 3) | 50.00% |
| Aminolevulinic acid hydrochloride | 10.00% |

In order to prepare phase 1, the water was introduced initially and heated to from 60 to 70° C., after which the Keltrol was dispersed in it in vacuo. The mixture was homogenized for 4 min at step 1, after which it was left to cool down to 30° C. while being stirred at step 1.

In order to prepare phase 2, the nanocarrier system was initially introduced in a sealed vessel, in vacuo and at room temperature, and the 5-aminolevulinic acid hydrochloride was completely dissolved in it over a period of from 2 to 3 h while the mixture was being stirred.

After that, phase 2 was mixed with phase 1 in vacuo and the whole was then gassed with nitrogen. The resulting composition was mixed to homogeneity while being stirred for 2 h at a temperature of at most 30° C.

In order to determine the long-term stability of the active compound, a portion of the gel was subjected to a storage test. After one year of storage at 5° C., the content of 5-ALA was 99.17% of the original content, while a value of 98.94% was obtained at room temperature over the same period of time.

3. Photodynamic Therapy Using the Nanocolloid Lotion Described in Example 1

The effect of the nanolotion according to the invention was investigated in a clinical study of 55 basal cell carcinomas in a group of patients consisting of 19 individuals.

Before the nanocolloid lotion was applied, the entire skin area to be treated was cleaned with an alcoholic solution. In each case 0.15 g of nanocolloid solution was applied per $cm^2$ of the skin area to be treated, resulting in a thin, visible film of lotion. After the lotion had been applied, the entire area was covered with a light-impermeable covering material in order to prevent the lotion smearing and to prevent any undesirable photodynamic reactions brought about by the light in the room. After a reaction time of 6 h, the covering was removed and the presence of protoporphyrin IX, and the extent of the tumor, were assessed on the basis of the characteristically red fluorescence of porphyrins when irradiated with ultraviolet light.

The irradiation was performed using unfiltered light from a 250 W halogen lamp having a spectral distribution over the entire visible range with a maximum of about 800 nm. All the lesions were irradiated at a distance of 10 cm, thereby enabling regions having a diameter of up to 10 cm to be irradiated. The time of irradiation was 20 min, and the intensity was 200 $mW/cm^2$, corresponding to a total light dose of 240 $J/cm^2$.

The group of patients comprised 19 individuals who had one or more superficial basal cell carcinomas without metastases. In all, 55 basal cell carcinomas were treated by photodynamic therapy. None of the patients included in this study had previously been treated either with a conventional method or with photodynamic therapy. The patients were aged from 32 to 93, with the average age being 65. 14 (73.7%) patients were male and 5 (25.3%) were female. With one exception, the skin tumors which were treated in this study were superficial lesions. The average diameter of the lesions was 13.2 mm, with the size varying between 4.0 and 45 mm. The number of tumors treated in the different body regions was 11 (20%) in the head and neck region, 37 (67%) in the trunk region, 3 (5%) on the upper limbs and 4 (7%) on the lower limbs. Before the treatment was initiated, biopsies were routinely removed for confirming the diagnosis. The success of the therapy was assessed by visual inspection and palpation and, in the case of 26 (47%) of the tumors, by histopathological investigations as well. The absence of a clinically detectable tumor at the treatment site at the time of the post irradiation examination was defined as being a complete tumor response. A perceptible reduction in the size of the tumor was defined as being a partial tumor response.

The response rates which were achieved in this study are summarized in table 5. It was found that 47 (85%) of the 55 basal cell carcinomas treated in the 19 patients regressed completely after one single treatment, as was confirmed clinically by subsequent investigation performed at least 6 months after the treatment. The remaining 8 (15%) basal cell carcinomas were found to have regressed partially, i.e. there was a perceptible reduction in the size of the tumors.

Table 6 shows how the results of the photodynamic therapy varied with the location of the basal cell carcinomas. The best results were obtained for the seven limb lesions, all of which regressed completely. Of the 37 trunk lesions, 32 tumors regressed completely, while 8 (76%) of the 11 tumors in the head and neck region also regressed completely.

TABLE 5

|  | Visual assessment | Biopsy |
| --- | --- | --- |
| Number of patients | 19 | 13 |
| Basal cell carcinomas | 55 | 26 |
| Complete regression | 47 (85%) | 21 (81%) |
| Partial regression | 8 (15%) | 5 (19%) |
| No reaction | — | — |

TABLE 6

|  | Head and neck | Trunk | Limbs |
| --- | --- | --- | --- |
| Number of patients | 6 | 12 | 4 |
| Basal cell carcinomas | 11 | 37 | 7 |
| Complete regression | 8 (73%) | 32 (86%) | 7 (100%) |
| Partial regression | 3 (27%) | 5 (14%) | — |
| No reaction | — | — | — |

4. Photodynamic Therapy Using the Nanocolloid Gel Described in Example 2

The effect of the nanoemulsion according to the invention in the form a gel was investigated in a clinical study of the photodynamic therapy of condylomata acuminata and intraepithelial neoplasia of the vulva (VIN) as performed on 47 lesions in a group of patients consisting of 16 individuals aged from 18 to 45 (average age, 32.7).

The gel was applied as described for the lotion in example 3 except that the incubation time allowed for diffusing the 5-aminolevulinic acid was only 90 min. Irradiation was carried out using an argon dye laser (Coherent Innova, Model 310, Palo Alto, Calif.) with monochromatic light (630 nm) and with light doses of between 50 J/cm$^2$ and 125 J/cm$^2$.

After one single treatment, nine of the 16 patients showed complete regression, while the other seven showed partial regression, during a post-irradiation examination period of between 1 and 12 months. The treatment was well tolerated by the majority of the group of patients. The patients were free to interrupt the irradiation if the pain became excessive. The number of interruptions which occurred prior to the complete radiation time being reached was recorded. Only three of the patients had interrupted the irradiation more than five times, while five of the patients interrupted the irradiation once or twice; the remaining patients did not require any interruption.

What is claimed is:

1. A composition comprising a nanoemulsion which comprises an active substance which can be converted into protoporphyrin IX, the active substance being selected from the group consisting of at least one of 5-aminolevulinic acid, a salt compound thereof, a complex compound thereof, an addition compound thereof, precursors thereof, and metabolites thereof, and (b) a carrier in an aqueous phase, with the carrier being formed from at least one lipid and from at least one emulsifier comprising soybean lecithin.

2. The composition of claim 1, wherein the average size of the emulsified particles is from 10 to 200 nm.

3. The composition of claim 1 wherein the active substance is present in a proportion of from 1 to 25% by weight based on the total weight of the composition.

4. The composition of claim 1 wherein the composition additionally comprises adjuvants and/or additives which are customary in cosmetics or pharmacy.

5. The composition of claim 4 wherein the composition is present in the form of a gel and, based on the total weight of the composition, comprises from 5 to 15% of active substance, from 45 to 55% of carrier and from 1 to 5% of adjuvants, with the remainder being water.

6. The composition of claim 4 wherein the composition is present in the form of a lotion and, based on the total weight of the composition, comprises from 5 to 15% of active substance, from 15 to 25% of carrier and from 15 to 25% of adjuvants, with the remainder being water.

7. The composition of claim 1 wherein the content of active substance is reduced by not more than 5% after one year of storage at room temperature.

8. The composition of claim 1 wherein the composition is in the form of a pharmaceutical preparation.

9. The composition of claim 8 wherein the composition can be applied topically.

10. A kit which comprises a topically applicable composition as claimed in claim 9 and at least one component selected from the group consisting of:

(a) an essentially light-impermeable sheet-like material, (b) means for attaching the sheet-like material to a site of application, and (c) means for applying the composition to a site of application.

11. A process for preparing a composition as claimed in claim 1 wherein a mixture comprising a carrier and an aqueous phase is prepared and converted into a nanoemulsion, with the active substance being added before and/or after the conversion into the nanoemulsion, and, after that, adjuvants and/or additives are admixed where appropriate.

12. The process of claim 11, process is carried out while excluding oxygen and/or light.

13. The process of claim 11 wherein the process is carried out at a temperature of from 5 to 45° C.

14. A method of photodynamic therapy comprising topically applying a nanoemulsion that contains the composition of claim 1; then incubating in order to allow the composition of claim 1 to penetrate into tissue that is being treated; then irradiating the tissue with radiation.

15. The method of claim 14 wherein the tissue being treated has a disease associated with cell proliferation.

16. The method of claim 15, wherein the disease is a tumor disease.

17. The method of claim 16, wherein the disease is a basal cell carcinoma, a squamous cell carcinoma, Bowen's disease, solar keratosis, condylomata acuminata (CIN), intraepithelial neoplasia of the vulva (VIN), or a nodose or subcutaneous cancer disease.

18. The method of claim 15, wherein the disease is psoriasis.

19. A process for photodynamic therapy, wherein a composition as claimed in claim 1 is administered in an effective quantity to a diseased organism, incubation is performed for a period which is suitable for ensuring that an adequate quantity of the active substance is present in the tissue being treated, and thereafter the tissue is irradiated with light.

20. A method for detecting proliferating cells comprising selectively concentrating a photosensitizer that is produced by metabolism of the composition of claim 1 in proliferating cells as compared with normal cells; and then determining an extent to which the photosensitizer has been concentrated.

21. The method of claim 20 wherein proliferating cells are those of tumor diseases.

* * * * *